(12) United States Patent
Alkassar

(10) Patent No.: US 11,229,785 B2
(45) Date of Patent: Jan. 25, 2022

(54) CIRCULATORY ASSISTANCE DEVICE

(71) Applicant: Friedrich-Alexander-Universität Erlangen-Nürnberg, Erlangen (DE)

(72) Inventor: Muhannad Alkassar, Nuremberg (DE)

(73) Assignee: Friedrich-Alexander-UniversitätErlangen-Nürnberg, Erlangen (DE)

(*) Notice: Subject to any disclaimer, the term of this patent is extended or adjusted under 35 U.S.C. 154(b) by 0 days.

(21) Appl. No.: 16/328,538

(22) PCT Filed: Aug. 25, 2017

(86) PCT No.: PCT/EP2017/071422
§ 371 (c)(1),
(2) Date: Feb. 26, 2019

(87) PCT Pub. No.: WO2018/037111
PCT Pub. Date: Mar. 1, 2018

(65) Prior Publication Data
US 2019/0201602 A1 Jul. 4, 2019

(30) Foreign Application Priority Data
Aug. 26, 2016 (DE) ...................... 10 2016 115 940.9

(51) Int. Cl.
*A61M 1/12* (2006.01)
*A61M 60/268* (2021.01)
(Continued)

(52) U.S. Cl.
CPC ........ *A61M 60/268* (2021.01); *A61M 60/148* (2021.01); *A61M 60/40* (2021.01); *A61M 60/50* (2021.01)

(58) Field of Classification Search
None
See application file for complete search history.

(56) References Cited

U.S. PATENT DOCUMENTS

| 6,293,906 B1 | 9/2001 | Vanden Hoek et al. |
| 8,100,819 B2 | 1/2012 | Banik |

(Continued)

FOREIGN PATENT DOCUMENTS

| WO | WO 2004/075953 A1 | 9/2004 |
| WO | WO 2004/078025 A2 | 9/2004 |

OTHER PUBLICATIONS

English translation of the International Preliminary Report on Patentability issued in International Application No. PCT/EP2017/071422 dated Mar. 7, 2019.

*Primary Examiner* — Erica S Lee
(74) *Attorney, Agent, or Firm* — Hoffmann & Baron, LLP

(57) ABSTRACT

Circulatory assistance device for a heart of a living being, including a cuff for periodically applying pressure to the heart by at least one dielectric elastomer membrane which is controllable by a control device in synchronization with a cardiac beat in order to convey blood in pulses, wherein the cuff is designed to be pulled over the outside of the heart and for this purpose has an inner shape that is adapted to the outer contour of the heart at least in the region outside the ventricles, wherein the cuff is composed of an outer contraction layer including the dielectric elastomer membrane and an inner padding layer, and the inner padding layer is filled with an incompressible liquid and has at least one outlet valve, which is closed in a normal state and opened in an emergency state.

12 Claims, 5 Drawing Sheets

(51) Int. Cl.
    *A61M 60/40*     (2021.01)
    *A61M 60/148*     (2021.01)
    *A61M 60/50*     (2021.01)

(56) References Cited

U.S. PATENT DOCUMENTS

| | | | |
|---|---|---|---|
| 10,220,128 B1* | 3/2019 | Robinson | A61M 1/1068 |
| 2004/0010180 A1 | 1/2004 | Scorvo | |
| 2004/0249236 A1 | 12/2004 | Hegde et al. | |
| 2006/0129025 A1* | 6/2006 | Levine | A61B 17/00234 |
| | | | 600/37 |
| 2016/0346449 A1* | 12/2016 | Roche | A61M 60/40 |

* cited by examiner

CIRCULATORY ASSISTANCE DEVICE

CROSS-REFERENCE TO RELATED APPLICATIONS

This application is the U.S. National Phase of International Patent Application No. PCT/EP2017/071422, filed on 25 Aug. 2017, which claims benefit of German Patent Application No. 10 2016 115 940.9, filed on 26 Aug. 2016, the contents of which are incorporated herein by reference in their entirety.

BACKGROUND

Field

The invention relates to a circulatory assistance device for the heart of a living being.

Related Art

Each year about 300,000 adults in Germany become ill with heart failure. About one-third of these patients have such severe heart failure that they die within two years due to a lack of adequate treatment possibilities.

In children, congenital heart defects are the most frequent cause of cardiocirculatory diseases. The criteria used to evaluate the severity of the defect are cardiac function and structural abnormalities. The most common structural defects can be treated surgically. The selection of management options in cases of impaired cardiac function is very small. For a long time there was no possibility other than heart transplantation for adequate treatment in the case of life-threatening deterioration of cardiac function.

In recent years, various pump systems have been developed to support the function of the failing heart. All of these are mechanical pump units, which accelerate the blood in parallel with the working heart and thus indirectly relieve the burden on the heart.

Up to now, however, it has only been possible to compensate for weak pumping power of the heart by direct acceleration of the blood using an external pump. For this purpose, the blood, as the medium being delivered, must always come into contact with components of the pump (tubing system, pump unit, etc.). As a result of the strong activation of the coagulation system, this always results in a great increase in the risk for thrombus formation. Furthermore, the implantation of the input and output tubing systems in the large blood vessels increases the risk of sudden hemorrhage. A system of this type is very vulnerable and always serves only as an interim solution until heart transplantation or regeneration of the heart can take place, so it is not possible to discharge the patient from the hospital while still receiving this therapy.

From WO 2004/078025 A2, a circulatory assistance device is known in which a tubular blood vessel is surrounded by a cuff to which pressure can be applied from outside using an incompressible liquid, wherein pressure can be applied to the liquid with a separate pumping device in which a balloon volume is periodically compressed radially by an annular dielectric elastomer membrane. As a result, this fluid is conveyed into the cuff in pulses and thus constricts the blood vessel that it surrounds. The pump is controlled by a sensor for the cardiac cycle.

This device requires the implantation of two voluminous components in the human body, namely the cuff and the pump. In addition, the periodic radial compression of a blood vessel initially produces blood flow in both axial directions of the blood vessel, which makes it appear principally suited for use in veins with venous valves, but even there, interferes with the efficiency of the pump.

Dielectric elastomers consist of a highly incompressible, elastically deformable elastomer film (for example, made of silicone, natural rubber, polyurethane, or acrylic), covered on both sides with expandable electrodes. When power is applied to the electrodes, the elastomer undergoes reversible deformation, wherein the thickness of the elastomer film decreases and the elastomer film simultaneously elongates in both directions perpendicular to the thickness direction. When the current is interrupted, the elastomer returns to the initial state. In the case of an annular dielectric membrane, one of these two directions coincides with the circumferential direction of the ring, which means that an annular dielectric elastomer membrane has an enlarged diameter under the influence of electric power.

From US 2004/0249236 A1, a circulatory assistance device according to the preamble of claim 1 is known, which includes elongated dielectric elastomer membranes fastened such that the electrical energization thereof causes contraction of the cuff surrounding the heart. One drawback here is that the dielectric elastomer membranes are relatively short, and thus only small contraction strokes are possible. A second arrangement takes a lot of space outside of the heart, which is disadvantageous.

From US 2004/0010180 A1, a circulatory assistance device is known, including a membrane made of a meshwork of dielectric elastomer strands, resembling a stocking. A fluid-filled cavity for size adaptation may be located beneath the stocking. When power is lost, the cuff contracts and remains in this state, which can lead to an immediate, massive, life-threatening disturbance.

WO 2004/075953 A1 likewise discloses a circulatory assistance device according to the preamble of claim 1.

Peristaltic pumps using dielectric elastomer membranes positioned outside of the human or animal body are also known.

From U.S. Pat. No. 8,100,819 B2, the use of a dielectric elastomer membrane as an artificial annular closing muscle for the bladder, intestine or esophagus, as well as a patch fixable on the heart, is known.

In U.S. Pat. No. 6,293,906, a mesh-like jacketing for a pathologically enlarged heart is disclosed.

SUMMARY

The goal of the invention is to supply a circulatory assistance device of simple design that operates with high efficiency.

The invention arises from the features of claim 1. Advantageous developments and designs are the subject of the dependent claims. The problem is solved according to claim 1 in that a circulatory assistance device for a heart of a living being is supplied, including a cuff for periodically supplying pressure to the heart using at least one dielectric elastomer membrane that can be controlled by a control device in synchronization with a heart beat in order to convey blood in pulses, wherein the cuff is designed to be pulled over the outside of the heart and for this purpose has an inner shape that is adapted to the outer contour of the heart at least in the region outside the ventricles, wherein the cuff is composed of an outer contraction layer including the dielectric elastomer membrane and an inner padding layer, and the padding layer is filled with an incompressible liquid and has at least one outlet valve that is closed in a normal state and open in an emergency state.

The invention provides a mechanical system which specifically supports the heart in its pumping function using the structural characteristics of a diseased heart. Compared with conventional cardiac assistance pump systems, this has numerous advantages which allow long-term assistance for diseased hearts. Assistance of the heart's own pumping function by the cuff pulled over the outside of the heart does not entail any risk of bleeding or thrombosis tendencies. Because of the absence of an additional mechanical pump, it is not necessary to connect any expensive exterior apparatus to the patient. This results in a definite increase in the quality of life of the patient with heart disease. With the aid of the padding layer it is advantageously accomplished that in the case of a power loss, which represents an emergency state, the dielectric elastomer membrane which, when no electric power is being supplied, assumes the state of lower expansion, thus having a smaller circumference, does not constrict the heart, but instead the incompressible liquid located in the padding layer provided between the contraction layer and the wall of the heart can escape from the padding layer by the automatic opening of the outlet valve. Thus, this effect of the narrowed contraction layer can be avoided completely or partially. In the padding layer a membrane valve system is integrated, preferably in the area of connection with the heart, and if electric power is lost, this opens and leads to escape of the incompressible liquid. When the outlet valve is closed, the padding layer is deformable and follows the changes in shape of the elastomer membrane.

Long-term use of the cardiac assistance system is possible. Through the direct effect on the heart, higher efficacy can also be achieved, so that the power consumption per unit time is lower compared to conventional systems, and the circulatory assistance device according to the invention will thus be functional for a longer time with the available limited power supply. Thus, as long as a power supply device is also placed in the body, the patient will be independent of a charging process for a longer time, which will improve the quality of life.

A cuff that can be pulled over the heart according to a further embodiment is defined as a cuff applied in the area of the ventricle.

According to an alternative further embodiment, a cuff that can be pulled over the heart in the area is defined as a cuff that can be pulled over in the area of the ventricle and at least partially also in the area of at least one atrium, wherein the cuff must contain at least two dielectric elastomer membranes operating separately from one another, since application of pressure to the atria must take place at a different point within the cardiac cycle than the application of pressure to the ventricle.

In a particular further development, a dielectric elastomer membrane is supplied, including at least two partial membranes that are controlled in different ways by the control device. Here, a first partial membrane is located in the area of the atria (upper chambers of the heart) and a second partial membrane is located in the area of the ventricles (lower chambers of the heart). The different control pattern is achieved in that in coordination with the sinus node and/or atrial ventricular node stimulus, the two partial membranes are controlled in an anticyclic manner. The first and second partial membranes may be provided in the form of two separate elastomer membranes, each controlled by the control device over separate electrodes. Alternatively, the first and second partial membranes are provided using the same elastomer membrane, wherein the electrode layers are provided in an interrupted fashion and with their own power supply connections to form the partial membranes. Instead of two partial membranes, it is possible for three or four partial membranes to be provided.

According to an advantageous further development of this design, the padding layer has the thickness that corresponds to a difference in contractile movement of the contraction layer between an expanded state and a contracted state. In this way, interference with the heart activity due to loss of power is avoided completely, since the contraction layer in the non-energized state does not fit around the heart more closely than in the functional state, since the padding which empties thus forms a compressible buffer.

Preferably, the cuff is tulip-shaped to completely enclose the cardiac apex. In this way, a greater effect on the heart is achieved than in the case of merely an annular enclosure. With the tulip-shaped design, the area of the cuff provided for surrounding the cardiac apex narrows in the direction of the cardiac apex or ends in a closed apex, whereas the cuff widens in the area of the cardiac atria, in which region the heart also has a larger circumference.

According to an advantageous further development of the invention, the contraction layer includes a number of annular sections which can be electrically controlled separately in a time sequence. Thus, it is possible to accomplish supportive contraction of the membrane synchronously with the contraction of the heart muscle proceeding from the cardiac apex. Preferably 3 to 250, particularly 5 to 20 annular sections of the contraction layer are provided for this purpose. The control of the individual annular sections takes place in a time-staggered manner according to the predetermined typical propagation of the muscular contraction movement.

According to an advantageous further development of this design, the padding layer includes the same number of fluid-filled annular spaces which in each case are located below the annular contraction layer sections, wherein each annular section has its own outlet valve. The adjacent annular sections are preferably separated from one another by expandable separating partitions.

According to an advantageous further development of the invention, the padding layer communicates over the outlet valve with a collecting bag or an outlet line for transport outside of the body. In this way, the liquid located in the padding layer is prevented from entering the body cavity. However, if the liquid is selected as suitable for discharge into the chest cavity, such components can be dispensed with. Nonlimiting examples of suitable liquids are all physiologically compatible liquids, for example physiological saline, plasma expanders, for example those based on dextran, hydroxyethyl starch or gelatin, or additional liquids known to persons skilled in the art. The physiologically compatible liquid itself is preferably pharmacologically inactive.

According to an advantageous alternative further development of the invention, it is therefore provided that the incompressible liquid of the padding layer is physiologically compatible and can be released through the outlet valve into the body of the living being, especially into the chest cavity thereof. Advantageously, in this way no outlet line from the body need be supplied, which theoretically could always also represent a portal of entry for bacteria, substances or impurities.

According to a very particular embodiment, the incompressible and physiologically compatible liquid of the padding layer includes at least one substance with a positive inotropic effect. After opening of the outlet valve and subsequent release of the liquid into the body of the living being, thus generally into its chest cavity, the at least one substance with a positive inotropic effect provides at least a brief increase in cardiac performance. Thus, advantageously a blood pressure drop is combated, which precisely in the first moments after loss of the circulatory assistance device could result in life-threatening circulatory weakness. In addition, the body is thus given a signal to adjust to the fact that the body's natural heart must now provide all of the pumping capacity until the loss of the circulatory assistance device is compensated for in another way, medically, surgically, or with a medical device. Nonlimiting examples for substances with a positive inotropic effect are epinephrine, norepinephrine, cardiac glycosides such as digoxin, digitoxin or ouabain, active substances from the group of so-called calcium sensitizers such as levosimendan, active substances from the group of phosphodiesterase-3 inhibitors, for example 3-amino-5-(4-pyridinyl)2(1H)-pyridinone (amrinone), 6-[4-(1-cyclohexyl-1H-tetrazole-5-yl)butoxy]-3,4-dihydroquinolin-2-one (cilostazole), milrinone, or enoximone. The physiologically compatible liquid may also include combinations of two or more substances with positive inotropic action. Unless a standard quantity of a substance or substances with positive inotropic effect is present in the psychologically compatible liquid, the person skilled in the art can determine the choice and dosage of the substance or substances with positive inotropic effect as necessary depending on the age, weight, other medications, disease state, and possibly other parameters of the living being as needed.

According to an advantageous further development of the invention, the control device includes an emergency state determination unit, which identifies the emergency state when the power supply for the contraction layer falls below a minimum value for a predetermined or specifiable time period. In this way, it is possible to make sure that a loss of power is reliably detected, but on the other hand, a serious alarm is not triggered, since that would induce irreversible opening of the outlet valve, and thus would functionally eliminate the circulatory assistance device according to the invention. However, if no power or only inadequate power is supplied to through the valve, by way of the opened valve, this would lead to a loss of the liquid between the heart and the membrane, so that the now contracted membrane cannot impede the heart's own residual function.

In addition, the problem is solved by a circulatory assistance system including a control device, a circulatory assistance device according to one or more of the previous embodiments or further developments, a power supply device, and at least one sensor device for detecting the cardiac cycle.

The invention also relates to a medical procedure of introducing the circulatory assistance system explained above into the body of a living being, wherein the circulatory assistance device is pulled over the heart of the living being, fixed there, and the sensor device is attached to the heart.

The invention also relates to a method of assisting the circulation of a living being using the above-named circulatory assistance system, wherein the cardiac cycle of the heart is detected, and synchronously with this the contraction layer is supplied with power, so that the contraction of the elastomer layer works together with the contraction of the area of the muscle located beneath the elastomer layer. In this way, the pumping power of the heart can be improved in a patient with heart failure, and thus life expectancy and quality of life can be increased.

Further advantages, features, and details will become apparent from the description that follows, in which—in some cases, referring to the drawings—at least one exemplified embodiment is described in detail. Identical, similar, and/or functionally equivalent parts are provided with the same reference symbol.

DETAILED DESCRIPTION

Figure 1:
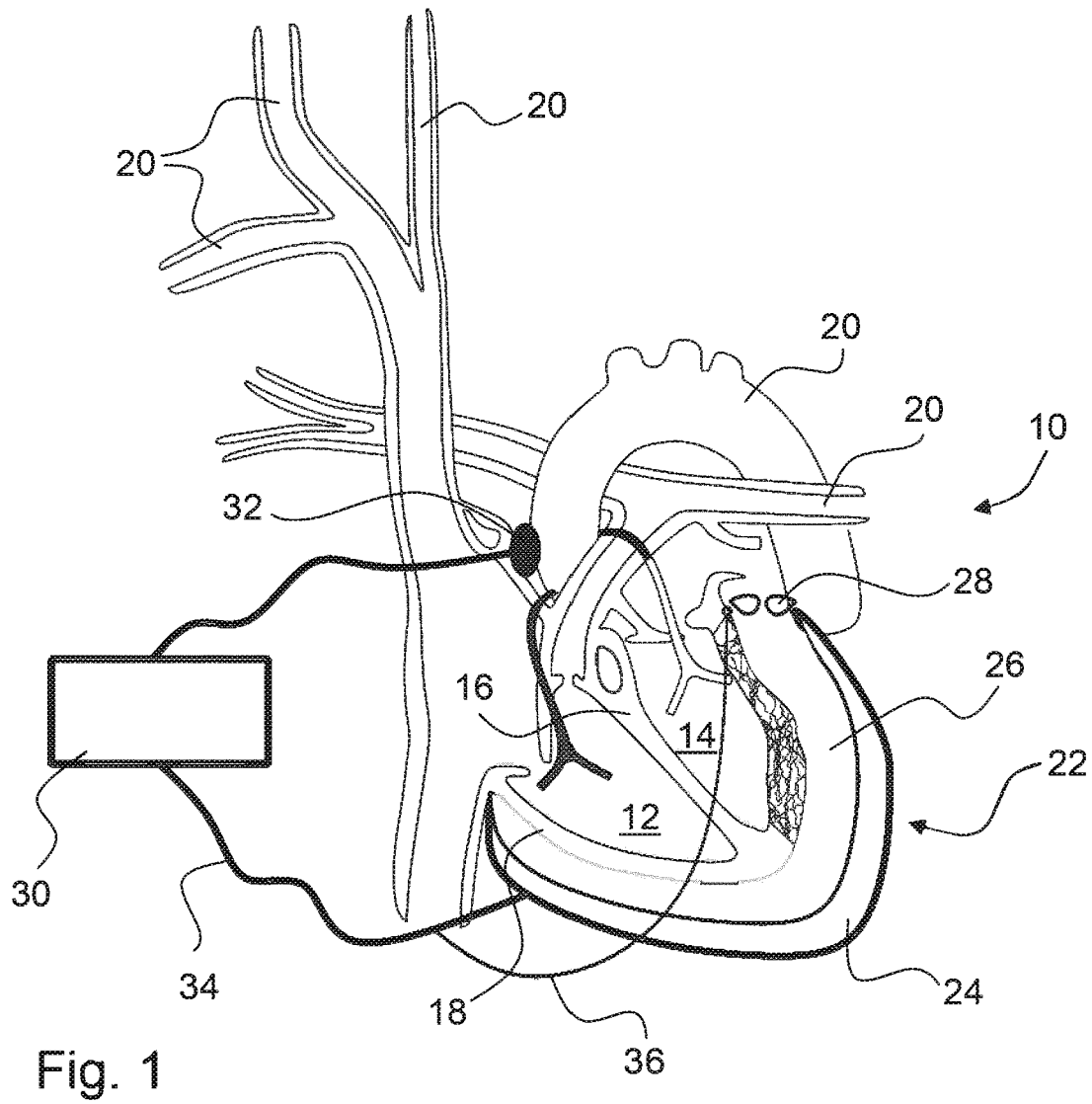
FIG. 1 is a schematic representation of a heart with a circulatory assistance system in the normal operating state.
Figure 2:
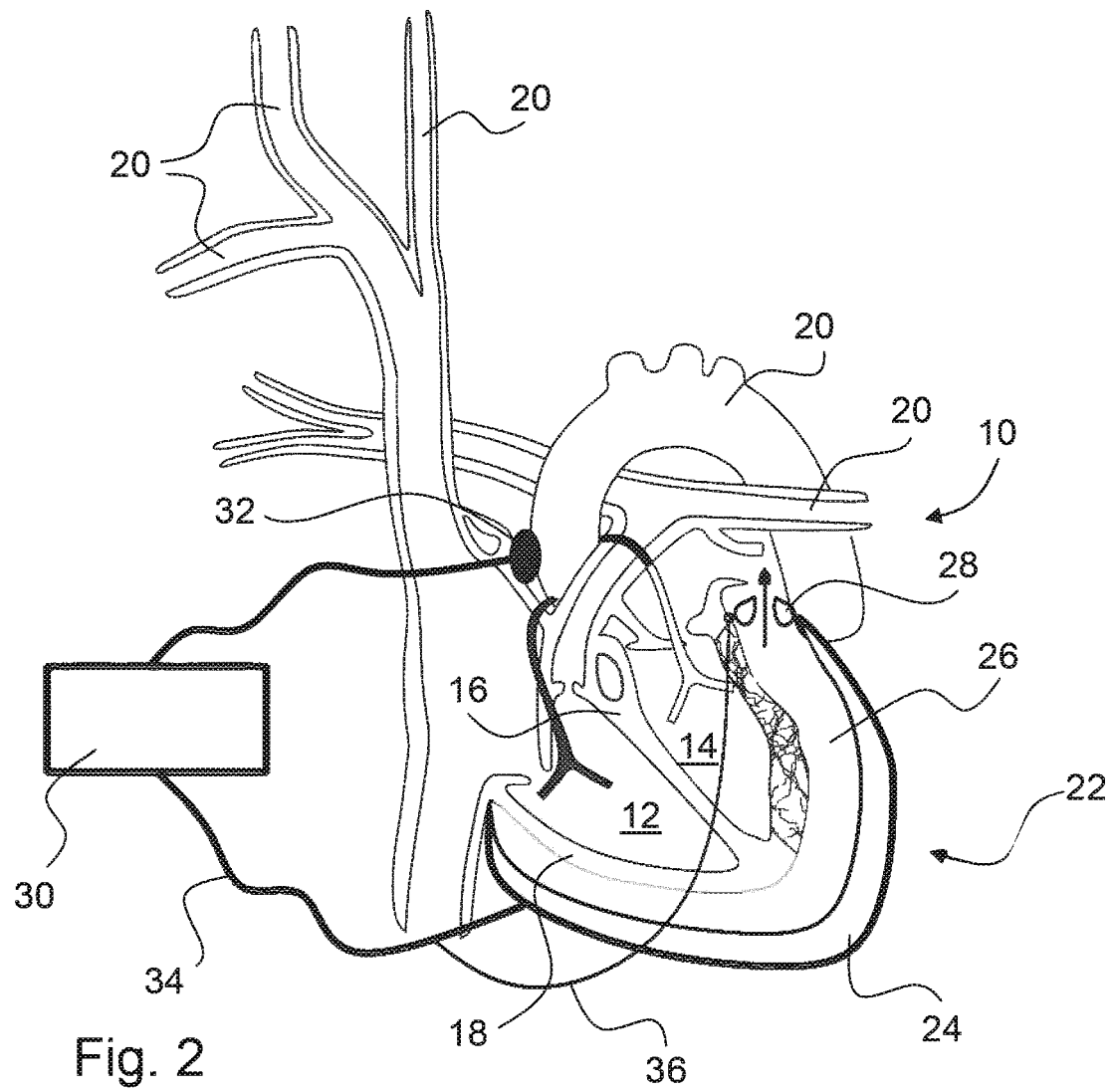
FIG. 2 is a schematic representation of a heart with the circulatory assistance system in an emergency state.

In FIGS. 1 and 2 a heart of a living being with a circulatory assistance system according to the present invention is shown in two states, namely in the normal operating state in FIG. 1 (first state) and in an emergency state in FIG. 2 (second state). The heart 10 consists essentially of a right ventricle 12, a left ventricle 14, an intraventricular septum 16, and a ventricular wall 18. Additional vessels 20 of the circulatory system are not shown in further detail or provided with reference symbols.

A cuff 22 of a circulatory assistance device in a first embodiment fits closely around the heart 10 during the diastolic phase of the cardiac cycle. The cuff includes an outer contraction layer 24 and an inner padding layer 26. In the interior of the contraction layer 24 there is at least one elastic elastomer membrane, which preferably has a closed annular shape, or as shown in FIGS. 1 and 2, a tulip shape. In the cuff 22, several dielectric elastomer membranes may be arranged adjacent to or one on top of the other. The elastomer membranes are preferably closed, but within the scope of the invention it is also possible to arrange several separately controlled annular elastomer membranes alongside one another.

Materials that may be considered for the contraction layer 24 include, for example, PDMS, polyurethane, and acrylates (e.g., VHB from 3M). Particularly suitable is a silicone with polydimethyl siloxane as the polymer component and acrylic polymers and natural rubber.

The inner padding layer 26 is functionally connected to an outlet valve 28 in such a way that in the opened state of the outlet valve 28, incompressible liquid located in the padding layer 26 can emerge into the environment or into reservoirs provided for this, not shown. In FIG. 1, the circulatory assistance device is in the normal operating state, so that the outlet valve 28 is closed.

The padding layer 26 preferably has a thickness of 0.5 cm to 2.5 cm and is preferably filled with an absorbable aqueous solution. According to a further development, this can also contain medication.

The circulatory assistance device is connected to a control device 30, which includes a power supply unit, not shown. The control device 30 is also connected to a sensor 32, which detects the cardiac cycle of the heart 10 at a suitable location. The control device 30 is connected to the contraction layer 24 over a power supply line 34, wherein sensor signals from sensors, not shown, indicating the state of the contraction layer 24 can also travel over separate conductors of the power supply line 34. From the power supply line 34, a power supply line 36 branches off; this supplies the outlet valve 28 with power such that it assumes the closed state shown in FIG. 1 when power is supplied. If the power supply unit of the control device 30 does not function, or in case of inadequate power supply to the contraction layer 24, the outlet valve 28 receives no power supply or only an inadequate one, and then it opens so that the incompressible liquid located in the padding layer 26 can flow over the outlet valve 28 into the environment, i.e., the surrounding tissue in the chest cavity, as is shown in FIG. 2.

Figure 3:
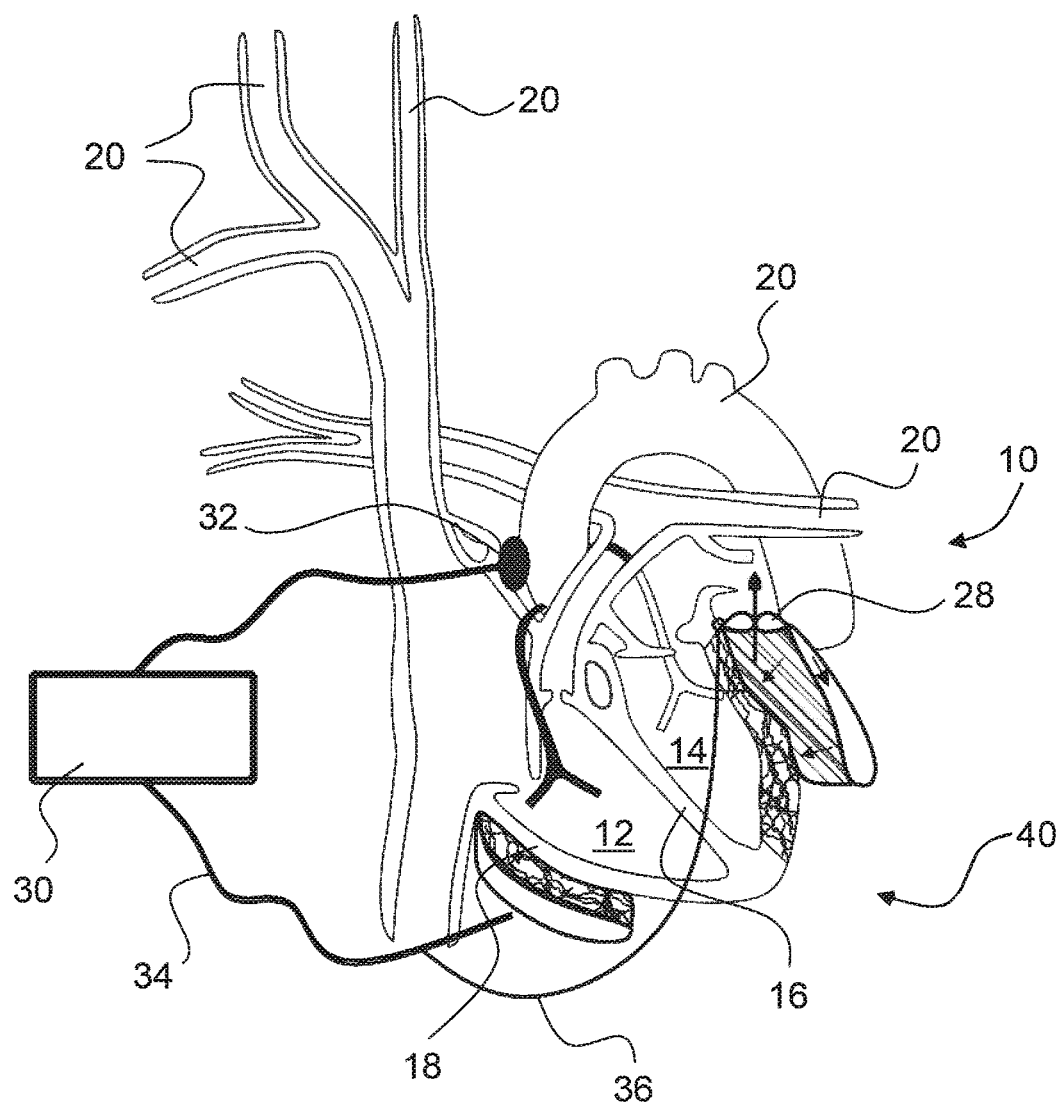
FIG. 3 is a schematic representation of a heart with a second design of a circulatory assistance system in the normal operating state.

In FIG. 3, a second embodiment of a circulatory assistance system in the form of an annular cuff 40 is shown. Aside from the fact that this cuff 40 does not surround the apex of the heart 10, this has structurally and functionally the same design as the cuff 22.

As can be seen in FIGS. 1 to 3, the cuff 22 or 40 preferably extends along the entire ventricular wall 18 and is fastened to it by means not shown, preferably mounted in an annular shape.

In normal operation the sensor 32 detects the cardiac cycle of the heart 10. In an initial state the heart 10 is in the diastolic phase, in which it is relaxed and occupies the largest volume, wherein the two ventricles fill with blood. In this state the contraction layer 24 is supplied with power so that this is in the state of greatest possible expansion. The padding layer 26 filled with an incompressible fluid at this time is located internally against the ventricular wall 18 and externally against the contraction layer 24. As soon as the control device 30 detects the beginning of systole, the power supply to the contraction layer is interrupted suddenly or according to a predetermined sequence, so that the contraction layer 24 thus draws together radially inward and transfers the resulting, radially inwardly directed forces to the ventricular wall 18 of the heart 10. At the latest when the systolic phase of the cardiac cycle is completed, the contraction layer 24 is again supplied with power, so that this again expands radially and with it, moves the padding layer 26 away from the expanding ventricular wall 18.

Both the power supply and the power interruption over line 34 can preferably take place according to a preset voltage-time curve.

Figure 4:
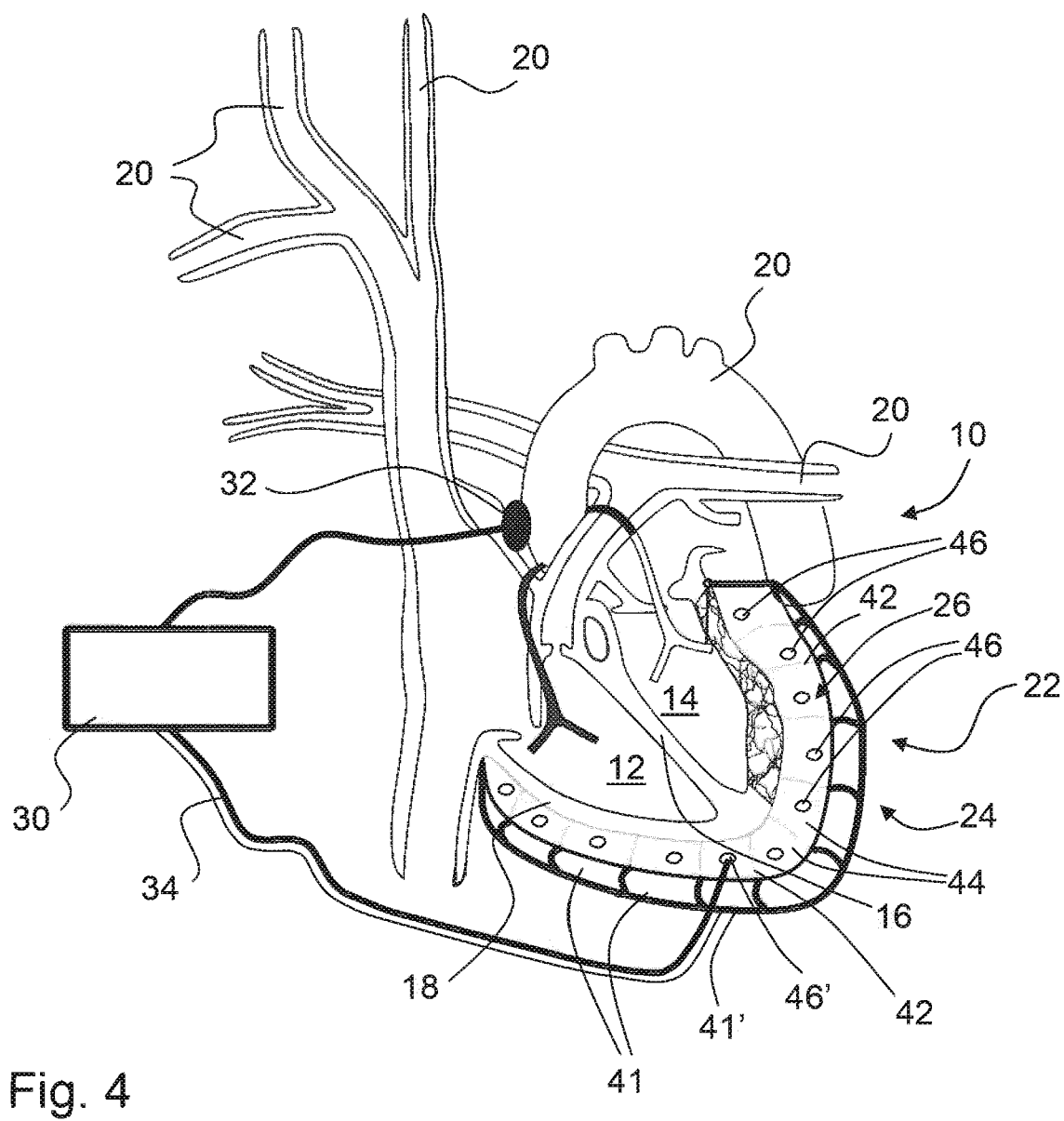
FIG. 4 is a schematic representation of a heart with a third design of a circulatory assistance system.

In FIG. 4, a third embodiment is shown, which differs from the previous embodiments in that the contraction layer 24 includes a number of adjacent annular sections 41, each of which is individually controlled by the control device 30, which for the sake of clarity is only shown for the annular section marked with reference symbol 41'. This is normally a film that is subdivided into rings. Alternatively, individual film rings connected together may be provided.

Correspondingly, the padding layer 26 located beneath it is subdivided into a number of adjacent annular regions 44 separated by expandable partitions 42. Each annular region 44 has its own outlet valve 46, controlled by the control device 30 (for the sake of clarity, only shown here for one outlet valve 46') into the environment.

The annular sections 41 are separately supplied with power by the control device 30 in a time-staggered sequence, synchronous with the cardiac contraction spreading from the cardiac apex. Thus, energization of the individual annular sections 41 takes place in a time-staggered manner in accordance with the typical spread of the muscular contractile movement of the heart.

Figure 5A:
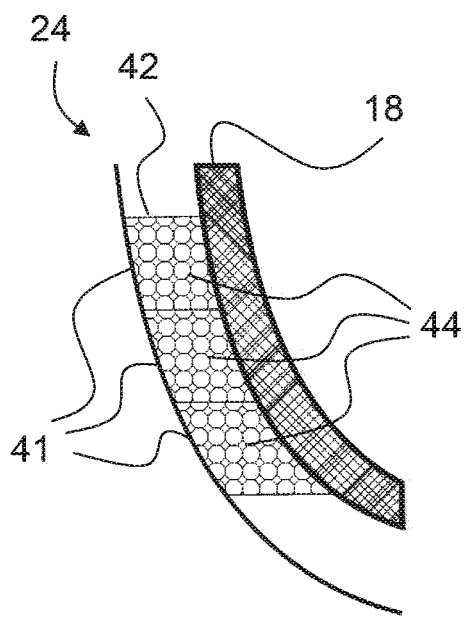
FIGS. 5a-5c are several views of the mode of action of the third embodiment.
Figure 5B:
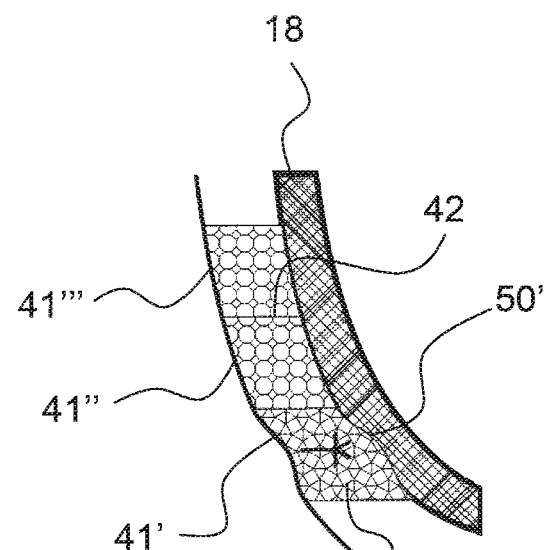
Figure 5C:
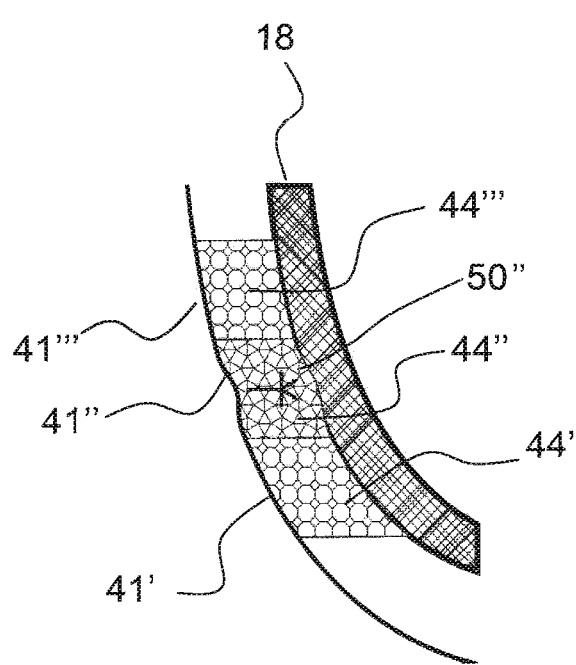

FIGS. 5a-5c show three schematic representations for demonstrating the functioning of the design according to FIG. 4. In FIG. 5a, the contraction layer 24 is shown in a resting position, in which all annular sections 41 are supplied with power. Correspondingly, no pressure is applied to the ventricular wall 18.

In FIG. 5b, the power supply to the first annular section 41' is interrupted, but not interrupted to the additional annular sections 41" and 41'". Thus, the first annular section 41' draws together and contracts. Since an incompressible medium is contained in the corresponding annular space 44', in this way a pressure is exerted on the ventricular wall 18 at location 50'.

In FIG. 5c, when the power supply to the first annular section 41' is restored and instead the power supply to the adjacent annular section 41" is interrupted, the first annular section 41' expands again and the pressure at location 50' of the ventricular wall 18 relaxes, while the second annular section 42" draws together and contracts, generating pressure on the ventricular wall 18 at location 50". All of this is controlled by the control device 30, specifically synchronously with the propagation of the cardiac contraction from the cardiac apex. In this way, one annular section 41 after the other is energized and thus a pressure wave is produced, which likewise propagates synchronously to the propagation of the cardiac contraction.

Although the invention was illustrated in greater detail and explained by preferred embodiments, the invention is not limited by the examples disclosed, and other variations can be derived from these by the person skilled in the art without leaving the scope of protection of the invention. From this it is clear that a number of possible variations exist. It is also clear that embodiments named by way of example only represent examples that are not in any way to be perceived as limiting, for example, the scope of protection, the possibilities of application or the configuration of the invention. Instead the above description and the explanation of the figures will place the person skilled in the art in a position to concretely implement the exemplified embodiments, in which the person skilled in the art, knowing the disclosed concept of the invention, can make many changes, for example in terms of the function or the arrangement of individual elements named in an exemplified embodiment, without leaving the scope of protection defined by the claims and their legal counterparts, for example further explanation in the description.

The invention claimed is:

1. A circulatory assistance device, the circulatory assistance device comprising:
　　a cuff configured to be pulled over an outside of a heart of a living being and having an inner shape that is adapted to an outer contour of the heart at least in a region outside ventricles of the heart, the cuff comprising:
　　　an inner padding layer filled with an incompressible liquid and comprising at least one outlet valve, the inner padding layer configured to be disposed over outside of the heart; and
　　　an outer contraction layer disposed over the inner padding layer, the outer contraction layer comprising at least one dielectric elastomer membrane; and
　　a control device configured to control the at least one dielectric elastomer membrane of the outer contraction layer in order to apply periodic pressure to the inner padding layer in synchronization with a heartbeat of the heart, wherein the control device is further configured to supply power to the at least one outlet valve of the inner padding layer so that the at least one valve is closed in a first state allowing the periodic pressure as applied to be in turn transmitted via the incompressible liquid of the inner padding layer to the heart so as to assist the heart in conveying blood in pulses, and wherein on failure to supply the power or supply of inadequate power by the control device the at least one outlet valve is open in a second state allowing discharge of the incompressible liquid from the inner padding layer through the at least one outlet valve so that pressure of the at least one dielectric elastomer membrane of the outer contraction layer as applied to the inner padding layer is not in turn transmitted by the inner padding layer to the heart and thus does not constrict the heart.

2. The circulatory assistance device according to claim 1, wherein the inner padding layer has a thickness that corresponds to a difference in contractile movement of the outer contraction layer between an expanded state and a contracted state.

3. The circulatory assistance device according to claim 1, wherein the outer contraction layer includes a plurality of annular sections, each annular section of the plurality of annular sections separately electrically controllable in a time-staggered sequence.

4. The circulatory assistance device according to claim 3, wherein the plurality of annular sections comprises 3 annular sections to 250 annular sections.

5. The circulatory assistance device according to claim 3, wherein the inner padding layer comprises a plurality of annular spaces that are liquid-filled and correspond respectively to the plurality of annular sections, in each case the plurality of annular spaces are located below the respective plurality of annular sections of the contraction layer, wherein each of the plurality of annular spaces has its own outlet valve.

6. The circulatory support device according to claim 1, wherein the inner padding layer communicates with a collecting bag through the at least one outlet valve or the at least one outlet valve and an outlet line for discharge of the incompressible liquid from the inner padding layer to the collecting bag.

7. The circulatory assistance device according to claim 1, wherein the incompressible liquid of the inner padding layer is physiologically tolerable and configured to be dischargeable through the at least one outlet valve into a body of the living being.

8. The circulatory assistance device according to claim 7, wherein the incompressible liquid of the inner padding layer comprises at least one substance with positive inotropic activity.

9. The circulatory assistance device according to claim 1, wherein the control device comprises a state detection unit configured to detect the second state when a power supply for the outer contraction layer falls below a minimum value for a specified time period.

10. A circulatory assistance system comprising a circulatory assistance device according to claim 1, wherein the control device comprises a power supply device, and at least one sensor device, the at least one sensor device configured to detect a cardiac cycle of the heart.

11. A method of introducing a circulatory assistance system into a body of a living being, the method comprising:
  pulling a circulatory assistance device over a heart of the living being, the circulatory assistance device comprising:
    a cuff configured to be pulled over an outside of the heart and having an inner shape that is adapted to an outer contour of the heart at least in a region outside ventricles of the heart, the cuff comprising an inner padding layer filled with an incompressible liquid and comprising at least one outlet valve, the inner padding layer configured to be disposed over outside of the heart, and an outer contraction layer disposed over the inner padding layer, the outer contraction layer comprising at least one dielectric elastomer membrane; and
    a control device configured to control the at least one dielectric elastomer membrane of the outer contraction layer in order to apply periodic pressure to the inner padding layer in synchronization with a heartbeat of the heart, wherein the control device is further configured to supply power to the at least one outlet valve of the inner padding layer so that the at least one valve is closed in a first state allowing the periodic pressure as applied to be in turn transmitted via the incompressible liquid of the inner padding layer to the heart so as to assist the heart in conveying blood in pulses, and wherein on failure to supply the power or supply of inadequate power by the control device the at least one outlet valve is open in a second state allowing discharge of the incompressible liquid from the inner padding layer through the at least one outlet valve so that pressure of the at least one dielectric elastomer membrane of the outer contraction layer as applied to the inner padding layer is not in turn transmitted by the inner padding layer to the heart and thus does not constrict the heart;
  fixing in position the circulatory assistance device pulled over the heart; and
  attaching a sensor device to the heart, the sensor capable of detecting a cardiac cycle of the heart.

12. A method of assisting circulation of the blood in a living being using a circulatory assistance system according to claim 10, wherein the method comprises:
  detecting a cardiac cycle of the heart using the sensor device; and
  supplying power to the outer contraction layer synchronously with the cardiac cycle of the heart as detected.

* * * * *